US 9,670,114 B2

(12) United States Patent
Tsai et al.

(10) Patent No.: US 9,670,114 B2
(45) Date of Patent: *Jun. 6, 2017

(54) METHODS AND APPARATUSES FOR REFORMING OF HYDROCARBONS INCLUDING RECOVERY OF PRODUCTS USING AN ABSORPTION ZONE

(71) Applicant: UOP LLC, Des Plaines, IL (US)

(72) Inventors: Robert Edison Tsai, Arlington Heights, IL (US); Xin X Zhu, Long Grove, IL (US); Tokhanh Ngo, Glendale Heights, IL (US); William Yanez, Crystal Lake, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 257 days.

This patent is subject to a terminal disclaimer.

(21) Appl. No.: 14/524,285

(22) Filed: Oct. 27, 2014

(65) Prior Publication Data
US 2016/0115098 A1  Apr. 28, 2016

(51) Int. Cl.
C01B 3/34 (2006.01)
C01B 3/52 (2006.01)
C07C 7/00 (2006.01)

(52) U.S. Cl.
CPC .............. C07C 7/005 (2013.01); C01B 3/34 (2013.01); C01B 3/52 (2013.01); C01B 2203/0227 (2013.01); C01B 2203/048 (2013.01); C01B 2203/0415 (2013.01); C01B 2203/1247 (2013.01)

(58) Field of Classification Search
None
See application file for complete search history.

(56) References Cited

U.S. PATENT DOCUMENTS

| 4,364,820 A | 12/1982 | DeGraff et al. |
| 4,673,488 A | 6/1987 | Turner et al. |
| 5,012,037 A | 4/1991 | Doshi et al. |

(Continued)

OTHER PUBLICATIONS

PCT Search Report dated Jan. 28, 2016 for corresponding PCT Application No. PCT/US2015/057138.

(Continued)

Primary Examiner — Tam M Nguyen

(57) ABSTRACT

Embodiments of apparatuses and methods for reforming of hydrocarbons including recovery of products are provided. In one example, a method comprises separating a reforming-zone effluent to form a net gas phase stream and a liquid phase hydrocarbon stream. The net gas phase stream is compressed, partially condensed and cooled to form a partially condensed, compressed net gas phase stream. The partially condensed, compressed net gas phase stream is separated to form an intermediate gas phase stream. The intermediate gas phase stream is cooled to form a cooled intermediate gas phase stream. The liquid phase hydrocarbon stream is cooled to form a cooled liquid phase hydrocarbon stream. The cooled intermediate gas phase stream is contacted with the cooled liquid phase hydrocarbon stream to form an $H_2$-rich stream and a cooled second intermediate liquid phase hydrocarbon stream that is enriched with $C_3/C_4$ hydrocarbons.

10 Claims, 2 Drawing Sheets

(56) References Cited

U.S. PATENT DOCUMENTS

| | | | |
|---|---|---|---|
| 5,238,555 A | | 8/1993 | Pappas et al. |
| 5,332,492 A | | 7/1994 | Maurer et al. |
| 5,411,721 A | | 5/1995 | Doshi et al. |
| 5,462,583 A | * | 10/1995 | Wood .................. B01D 53/14 585/809 |
| 5,792,897 A | * | 8/1998 | Rosser, Jr. ............ C10G 25/02 208/140 |
| 6,171,472 B1 | | 1/2001 | Lokhandwala et al. |
| 6,190,536 B1 | | 2/2001 | Lokhandwala et al. |
| 6,350,371 B1 | | 2/2002 | Lokhandwala et al. |
| 6,592,650 B2 | | 7/2003 | Pinnau et al. |
| 7,452,458 B2 | | 11/2008 | Sanchez et al. |
| 8,394,171 B2 | | 3/2013 | Elseviers et al. |
| 8,455,555 B2 | | 6/2013 | Allam et al. |
| 2005/0283038 A1 | * | 12/2005 | Kuechler ................. C07C 1/20 585/639 |
| 2006/0014990 A1 | * | 1/2006 | Kuechler ................. C07C 1/20 585/639 |
| 2016/0115100 A1 | * | 4/2016 | Glover ................... C07C 7/005 585/802 |

OTHER PUBLICATIONS

Mivechian et al., Performance Comparison of Different Separation Systems for H2 Recovery from Catalytic Reforming Unit Off-Gas Streams, Chemical Engineering and Technology, v 36, n 3, p. 519-527, Mar. 2013; ISSN: 09307516, E-ISSN: 15214125; DOI: 10.1002/ceat.201200558; Publisher: Wiley-VCH Verlag.

Allen, Managing Hydrogen Recovery, International Journal of Hydrocarbon Engineering (ISSN 1364-3177) V4 N.4 71-75 (Apr. 1999), v 4, n 4, p. 71-75, Apr. 1999; ISSN: 13643177; Publisher: Palladian Publications.

* cited by examiner

METHODS AND APPARATUSES FOR REFORMING OF HYDROCARBONS INCLUDING RECOVERY OF PRODUCTS USING AN ABSORPTION ZONE

TECHNICAL FIELD

The technical field relates generally to reforming of hydrocarbons, and more particularly relates to apparatuses and methods for reforming of hydrocarbons with improved recovery of products from a reforming-zone effluent.

BACKGROUND

High octane gasoline is needed for modern gasoline engines. Previously, octane numbers were often improved by incorporating various lead-containing additives into the gasoline. As lead-containing additives have been phased out of gasoline for environmental reasons, it has become increasingly necessary to rearrange the structure of the hydrocarbons used in gasoline blending to achieve higher octane ratings. Catalytic reforming of hydrocarbons is a process widely used by refiners for upgrading the octane ratings of gasoline as well as for other useful hydrocarbon conversion applications.

In catalytic reforming, a hydrocarbon feedstock of, for example, $C_5$ hydrocarbons to about $C_{11}$ hydrocarbons, is contacted with a reforming catalyst to convert at least a portion of the heavier hydrocarbons to aromatic hydrocarbons, for example, to increase the octane content of gasoline. The catalytic reforming of the heavier hydrocarbons to produce a reformate that includes aromatic hydrocarbons also produces significant quantities of valuable hydrogen and lighter hydrocarbons, such as liquefied petroleum gas (LPG) containing primarily $C_3$ and $C_4$ hydrocarbons. Refiners are looking for ways to maximize the recovery of reforming products, such as reformate, hydrogen and LPG, from the reforming reactor effluent.

Accordingly, it is desirable to provide apparatuses and methods for reforming of hydrocarbons with improved recovery of products from a reforming reactor effluent. Furthermore, other desirable features and characteristics will become apparent from the subsequent detailed description and the appended claims, taken in conjunction with the accompanying drawings and this background.

BRIEF SUMMARY

Apparatuses and methods for reforming of hydrocarbons including recovery of products are provided herein. In accordance with an exemplary embodiment, an apparatus for reforming of hydrocarbons including recovery of products comprises a separation zone. The separation zone is configured to receive and separate a reforming-zone effluent that comprises $H_2$, $C_4^-$ hydrocarbons, and $C_5^+$ hydrocarbons including aromatics to form a net gas phase stream that comprises $H_2$ and $C_6^-$ hydrocarbons and a liquid phase hydrocarbon stream that comprises $C_5^+$ hydrocarbons. A first compressor is configured to receive and compress the net gas phase stream to form a compressed net gas phase stream. A first cooler is configured to receive and partially condense and cool the compressed net gas phase stream to form a partially condensed, compressed net gas phase stream. A knockout drum is configured to receive and separate the partially condensed, compressed net gas phase stream into an intermediate gas phase stream and a first intermediate liquid phase hydrocarbon stream. A first chiller section is configured to receive and cool the intermediate gas phase stream to form a cooled intermediate gas phase stream. A second chiller section is configured to receive and cool the liquid phase hydrocarbon stream to form a cooled liquid phase hydrocarbon stream. An absorber is in fluid communication with the first chiller section and the second chiller section to correspondingly receive the cooled intermediate gas phase stream and the cooled liquid phase hydrocarbon stream. The absorber is configured for contacting the cooled intermediate gas phase stream with the cooled liquid phase hydrocarbon stream to extract $C_3/C_4$ hydrocarbons from the cooled intermediate gas phase stream to the cooled liquid phase hydrocarbon stream and to form an $H_2$-rich stream and a cooled second intermediate liquid phase hydrocarbon stream that is enriched with $C_3/C_4$ hydrocarbons and further comprises $C_5^+$ hydrocarbons.

In accordance with another exemplary embodiment, a method for reforming of hydrocarbons including recovery of products is provided. The method comprises the steps of separating a reforming-zone effluent that comprises $H_2$, $C_4^-$ hydrocarbons, and $C_5^+$ hydrocarbons including aromatics to form a net gas phase stream that comprises $H_2$ and $C_6^-$ hydrocarbons and a liquid phase hydrocarbon stream that comprises $C_5^+$ hydrocarbons. The net gas phase stream is compressed to form a compressed net gas phase stream. The compressed net gas phase stream is partially condensed and cooled to form a partially condensed, compressed net gas phase stream. The partially condensed, compressed net gas phase stream is separated into an intermediate gas phase stream and a first intermediate liquid phase hydrocarbon stream. The intermediate gas phase stream is cooled to form a cooled intermediate gas phase stream. The liquid phase hydrocarbon stream is cooled to form a cooled liquid phase hydrocarbon stream. The cooled intermediate gas phase stream is contacted with the cooled liquid phase hydrocarbon stream to extract $C_3/C_4$ hydrocarbons from the cooled intermediate gas phase stream to the cooled liquid phase hydrocarbon stream and to form an $H_2$-rich stream and a cooled second intermediate liquid phase hydrocarbon stream that is enriched with $C_3/C_4$ hydrocarbons and further comprises $C_5^+$ hydrocarbons.

In accordance with another exemplary embodiment, a method for reforming of hydrocarbons including recovery of products is provided. The method comprises the steps of contacting a gas phase stream that comprises $H_2$ and $C_6^-$ hydrocarbons with a liquid phase hydrocarbon stream that comprises $C_5^+$ hydrocarbons in an absorber to extract $C_3/C_4$ hydrocarbons from the gas phase stream into the liquid phase hydrocarbon stream and to form an $H_2$-rich stream and an intermediate liquid phase hydrocarbon stream. The $H_2$-rich stream comprises primarily $H_2$ and the intermediate liquid phase hydrocarbon stream is enriched with $C_3/C_4$ hydrocarbons and further comprises $C_5^+$ hydrocarbons. The intermediate liquid phase hydrocarbon stream is separated in a stabilizer to form a $C_5^+$ hydrocarbon-rich reformate stream that comprises primarily $C_5^+$ hydrocarbons and a stabilizer gas stream that comprises $H_2$ and $C_4^-$ hydrocarbons. At least a portion of the stabilizer gas stream is partially condensed and cooled to form a partially condensed stabilizer net gas stream. The partially condensed stabilizer net gas stream is separated in a separator to form a $C_3/C_4$ hydrocarbon-rich LPG stream that comprises primarily $C_3/C_4$ hydrocarbons and a light ends gas stream that comprises primarily $H_2$ and $C_2^-$ hydrocarbons.

BRIEF DESCRIPTION OF THE DRAWINGS

The various embodiments will hereinafter be described in conjunction with the following drawing figures, wherein like numerals denote like elements, and wherein.

DETAILED DESCRIPTION

Figure 1:
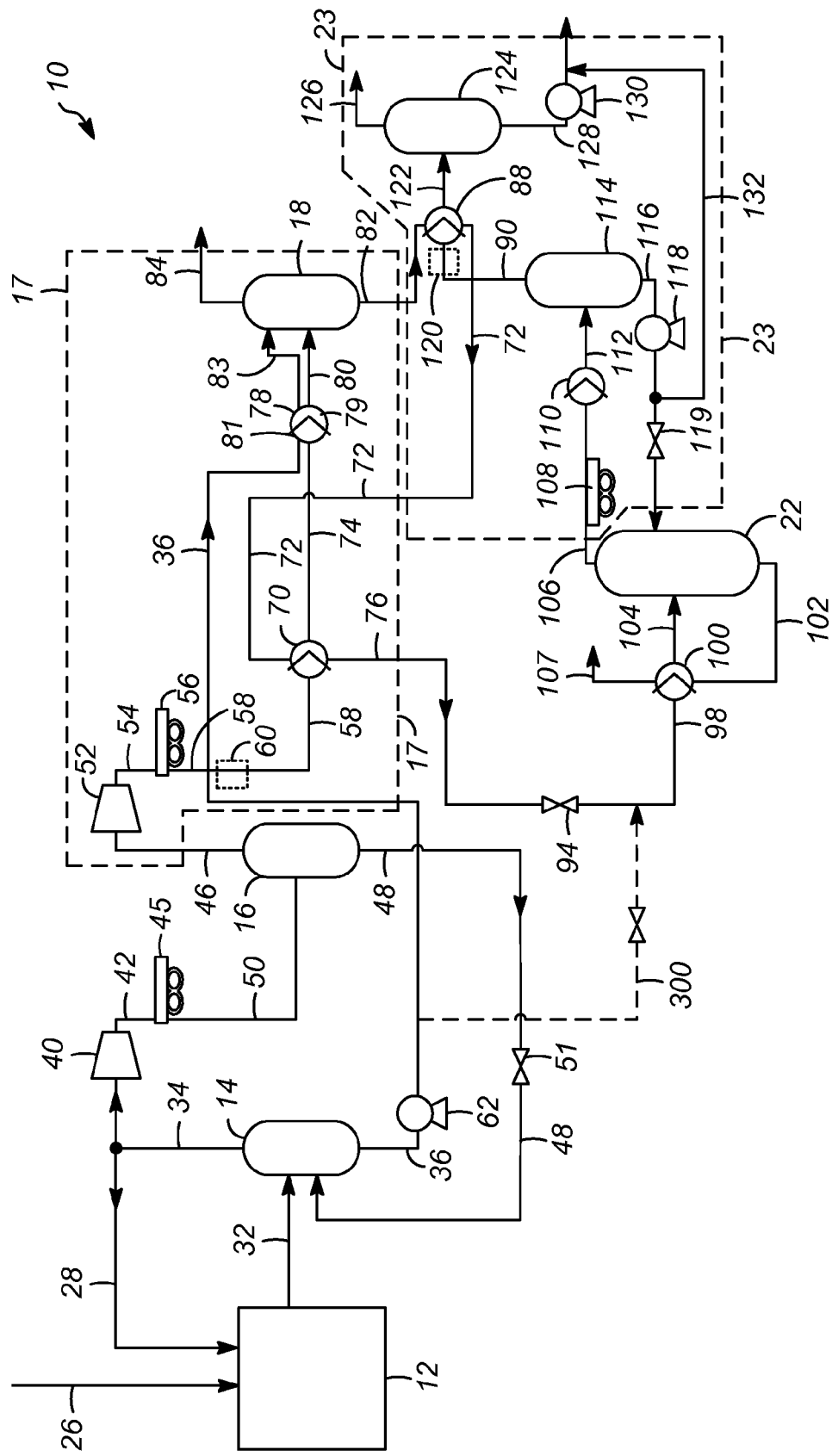
FIG. 1 schematically illustrates an apparatus and a method for reforming of hydrocarbons including recovery of products in accordance with an exemplary embodiment.

The following Detailed Description is merely exemplary in nature and is not intended to limit the various embodiments or the application and uses thereof. Furthermore, there is no intention to be bound by any theory presented in the preceding background or the following detailed description.

Various embodiments contemplated herein relate to apparatuses and methods for reforming of hydrocarbons with improved recovery of products from a reforming-zone effluent. The exemplary embodiments taught herein provide a separation zone configured to receive a reforming-zone effluent. As used herein, the term "zone" refers to an area including one or more equipment items and/or one or more sub-zones. Equipment items can include one or more reactors or reactor vessels, scrubbers, strippers, fractionators or distillation columns, absorbers or absorber vessels, regenerators, heaters, exchangers, coolers/chillers, pipes, pumps, compressors, controllers, and the like. Additionally, an equipment item can further include one or more zones or sub-zones. The reforming-zone effluent comprises hydrogen ($H_2$), $C_4^-$ hydrocarbons, and $C_5^+$ hydrocarbons including aromatics. As used herein, $C_x$ means hydrocarbon molecules that have "X" number of carbon atoms, $C_x^+$ means hydrocarbon molecules that have "X" and/or more than "X" number of carbon atoms, and $C_x^-$ means hydrocarbon molecules that have "X" and/or less than "X" number of carbon atoms.

The separation zone separates the reforming-zone effluent to form a net gas phase stream and a liquid phase hydrocarbon stream. The net gas phase stream comprises $H_2$ and $C_6^-$ hydrocarbons and the liquid phase hydrocarbon stream comprises $C_5^+$ hydrocarbons. In an exemplary embodiment, the net gas phase stream is compressed and partially condensed and cooled to form a partially condensed, compressed net gas phase stream. In an exemplary embodiment, a knockout drum separates the partially condensed, compressed net gas phase stream into a first intermediate liquid phase hydrocarbon stream that is recycled back to the separation zone and an intermediate gas phase stream.

The intermediate gas phase stream and the liquid phase hydrocarbon stream are passed along to an absorption zone. In an exemplary embodiment, the absorption zone comprises an absorber and first and second chiller sections that are upstream from the absorber. The first chiller section receives and cools the intermediate gas phase stream to form a cooled intermediate gas phase stream. The second chiller section receives and cools the liquid phase hydrocarbon stream to form a cooled liquid phase hydrocarbon stream. In an exemplary embodiment, the cooled intermediate gas phase stream and the cooled liquid phase hydrocarbon stream are introduced to the absorber as separate streams. In the absorber, the cooled intermediate gas phase stream contacts the cooled liquid phase hydrocarbon stream, for example, in countercurrent flow, to extract $C_3/C_4$ hydrocarbons from the cooled intermediate gas phase stream to the cooled liquid phase hydrocarbon stream and to form an $H_2$-rich stream and a cooled second intermediate liquid phase hydrocarbon stream. As used herein, the term "rich" means the corresponding component(s) is present in an amount of about 70 mole % or greater, such as about 80 mole % or greater. The cooled second intermediate liquid phase hydrocarbon stream is enriched with $C_3/C_4$ hydrocarbons and further comprises $C_5^+$ hydrocarbons including aromatics. As used herein, the term "enriched" means that the concentration of the corresponding component(s) has increased relative to its original or previous concentration.

In an exemplary embodiment, at least a portion of the cooled second intermediate liquid phase hydrocarbon stream is passed through at least one heater and/or heat exchanger(s) to form a heated second intermediate liquid phase hydrocarbon stream. The heated second intermediate liquid phase hydrocarbon stream is separated in a stabilizer to form a $C_5^+$ hydrocarbon-rich reformate stream that comprises primarily $C_5^+$ hydrocarbons including aromatics and a stabilizer gas stream that comprises $H_2$ and $C_4^-$ hydrocarbons. As used herein, the term "primarily" means about 50 mole percent (mole %) or greater. A stabilizer gas separation zone partially condenses, cools and further separates at least a portion of the stabilizer gas stream to form a $C_3/C_4$ hydrocarbon-rich LPG stream that comprises primarily $C_3/C_4$ hydrocarbons and a light ends gas stream that comprises $H_2$ and $C_2^-$ hydrocarbons.

Referring to FIG. 1, an apparatus 10 for reforming of hydrocarbons in accordance with an exemplary embodiment is provided. The apparatus 10 comprises a reforming zone 12, a separation zone 14, a knockout drum 16, an absorption zone 17 including an absorber 18 (e.g., multi-stage vessel or separation vessel that contains trays or packing), a stabilizer 22, and a stabilizer gas separation zone 23 that are in fluid communication.

In an exemplary embodiment, a reforming-zone feedstock 26 containing naphtha fraction hydrocarbons, such as from $C_5$ to about $C_{11}$ hydrocarbons with a boiling point range of, for example, from about 70 to about 205° C., is introduced to the apparatus 10. The reforming-zone feedstock 26 and a recycle net gas phase stream 28 (discussed in further detail below) are passed along to the reforming zone 12 that contains a reforming catalyst as is well-known in the art. The reforming zone 12 will typically comprise a plurality of stacked or side-by-side reactors with provisions for intermediate heating of the intermediate reactant stream (e.g., the reforming-zone feedstock 26 and the recycle net gas phase stream 28 including any conversion products formed therefrom) and one or more heat exchangers. In an exemplary embodiment, in the reforming zone 12, the recycle net gas phase stream 28 is combined with the reforming-zone feedstock 26 for contact with the reforming catalyst.

A reforming-zone effluent 32 is formed in the reforming zone 12 and contains $H_2$, $C_5^+$ hydrocarbons including aromatics, and lighter hydrocarbons such as $C_4^-$ hydrocarbons including $C_3$ and $C_4$ hydrocarbons. In an exemplary embodiment, the reforming-zone effluent 32 is a two-phase liquid-gas stream in which $H_2$ and the lighter hydrocarbons (e.g., $C_4^-$ hydrocarbons) are predominately in the gas phase and the heavier hydrocarbons (e.g., $C_5^+$ hydrocarbons including aromatics) are predominately in the liquid phase. In one embodiment, the reforming-zone effluent 32 has a temperature of from about 35 to about 50° C. and, independently, a pressure of from about 240 to about 830 kPa gauge.

The reforming-zone effluent 32 is introduced to the separation zone 14. The separation zone 14 separates the reforming-zone effluent 32 into net gas phase stream 34 and a liquid phase hydrocarbon stream 36. In an exemplary embodiment, the net gas phase stream 34 comprises $H_2$ and $C_6^-$ hydrocarbons and the liquid phase hydrocarbon stream 36 comprises $C_5^+$ hydrocarbons including aromatics. In one example, the net gas phase stream 34 comprises $H_2$ present in an amount of from about 80 to about 90 mole %, $C_1$ hydrocarbons present in an amount of about 2 to about 5 mole %, $C_2$ hydrocarbons present in an amount of from about 2 to about 5 mole %, $C_3$ hydrocarbons present in an amount of from about 2 to about 4 mole %, $C_4$ hydrocarbons present in an amount of from about 1.5 to about 2.5 mole %, and some $C_5^+$ hydrocarbons. In another example, the liquid phase hydrocarbon stream 36 comprises $C_5^+$ hydrocarbons present in an amount of from about 90 to about 99.9 mole % and some $C_4^-$ hydrocarbons and $H_2$. In an exemplary embodiment, the separation zone 14 is operated at a temperature of from about 35 to about 50° C. and, independently, a pressure of from about 240 to about 830 kPa gauge.

In an exemplary embodiment, a portion of the net gas phase stream 34 is passed back to the reforming zone 12 as the recycle net gas phase stream 28 as discussed above and a remaining portion of the net gas phase stream 34 is passed along to a compressor 40. The compressor 40 compresses the net gas phase stream 34 to form a compressed net gas phase stream 42. In an exemplary embodiment, the compressed net gas phase stream 42 has a temperature of from about 120 to about 150° C. and, independently, a pressure of from about 720 to about 2,490 kPa gauge.

The compressed net gas phase stream 42 is passed along to a cooler 45. In the cooler 45, the compressed net gas phase stream 42 is partially condensed and cooled to form a partially condensed, compressed net gas phase stream 50. In an exemplary embodiment, the partially condensed, compressed net gas phase stream 50 has a temperature of from about 30 to about 65° C. and, independently, a pressure of from about 690 to about 2,460 kPa gauge.

The partially condensed, compressed net gas phase stream 50 is introduced to the knockout drum 16. The knockout drum 16 separates the partially condensed, compressed net gas phase stream 50 into an intermediate gas phase stream 46 and an intermediate liquid phase hydrocarbon stream 48. In an exemplary embodiment, the intermediate gas phase stream 46 comprises $H_2$ and $C_6^-$ hydrocarbons and the intermediate liquid phase hydrocarbon stream 48 comprises $C_3^+$ hydrocarbons. In an exemplary embodiment, the intermediate liquid phase hydrocarbon stream 48 is passed through a valve 51 and recycled back to the separation zone 14 for further separation.

The intermediate gas phase stream 46 is introduced to the absorption zone 17. The liquid phase hydrocarbon stream 36 exits the separation zone 14 and is introduced to the absorption zone 17, and is passed through a pump 62. In an exemplary embodiment, the absorption zone 17 is configured as a countercurrent gas and liquid phase absorption zone for further separating $H_2$, $C_3/C_4$ hydrocarbons, and/or $C_5^+$ hydrocarbons via extraction and/or absorption by contacting the liquid and gas phase fractions of the intermediate gas phase stream 46 and the liquid phase hydrocarbon stream 36. As illustrated, in an exemplary embodiment, the absorption zone 17 comprises a single absorber 18 as well as other types of equipment items as will be described in further detail below. Alternatively, the absorption zone 17 may have more than one absorber as well as other types of equipment items.

In the absorption zone 17, the intermediate gas phase stream 46 is passed along to a compressor 52. The compressor 52 compresses the intermediate gas phase stream 46 to form a compressed intermediate gas phase stream 54. In an exemplary embodiment, the compressed intermediate gas phase stream 54 has a temperature of from about 120 to about 160° C. and, independently, a pressure of from about 1,980 to about 5,580 kPa gauge.

The compressed intermediate gas phase stream 54 is passed along to a cooler 56. In the cooler 56, the compressed intermediate gas phase stream 54 is partially cooled to form a partially cooled, compressed intermediate gas phase stream 58. In an exemplary embodiment, the partially cooled, compressed intermediate gas phase stream 58 has a temperature of from about 30 to about 65° C. and, independently, a pressure of from about 1,950 to about 5,550 kPa gauge.

Optionally, in an exemplary embodiment, the absorption zone 17 includes a dryer 60 (e.g., vessel with adsorbent material or the like adsorbing water or otherwise removing water) for removing water from the partially cooled, compressed intermediate gas phase stream 58 to help avoid the formation of hydrates. In an exemplary embodiment, upstream from the dryer 60, the partially cooled, compressed intermediate gas phase stream 58 includes water present in an amount of about 15 ppm by weight or greater, and after being passed through the dryer 60, the partially cooled, compressed intermediate gas phase stream 58 includes water present in an amount of less than about 15 ppm by weight.

After optional drying, the partially cooled, compressed intermediate gas phase stream 58 is passed along to an absorption zone heat exchanger 70 for indirect heat exchange with a partially heated intermediate liquid phase hydrocarbon stream 72 to form a further partially cooled, compressed intermediate gas phase stream 74 and a partially heated intermediate liquid phase hydrocarbon stream 76, respectively. Although the partially cooled, compressed intermediate gas phase stream 58 is illustrated as being cooled by the absorption zone heat exchanger 70, alternatively the partially cooled, compressed intermediate gas phase stream 58 can be passed through a cooler to form the further partially cooled, compressed intermediate gas phase stream 74 while the partially heated intermediate liquid phase hydrocarbon stream 72 can be passed through a separate heater to form the partially heated intermediate liquid phase hydrocarbon stream 76. In an exemplary embodiment, the further partially cooled, compressed intermediate gas phase stream 74 has a temperature of from about 10 to about 40° C. and, independently, a pressure of from about 1,920 to about 5,520 kPa gauge. In an exemplary embodiment, the partially heated intermediate liquid phase hydrocarbon stream 76 has a temperature of from about 60 to about 150° C. and, independently, a pressure of from about 1,830 to about 5,430 kPa gauge.

In an exemplary embodiment, the further partially cooled, compressed intermediate gas phase stream 74 is passed along to a dual-bundle chiller 78 that has a chiller section 79 and a chiller section 81 each configured for cooling. The further partially cooled, compressed intermediate gas phase stream 74 is passed through the chiller section 79 to further cool the stream 74 and form a cooled, compressed intermediate gas phase stream 80. In an exemplary embodiment, the cooled, compressed intermediate gas phase stream 80 has a temperature of from about −28 to about 4° C., such as about −12 to about 0° C. and, independently, a pressure of from about 1,890 to about 5,490 kPa gauge.

As illustrated, the liquid phase hydrocarbon stream 36 is introduced to the dual-bundle chiller 78. The liquid phase hydrocarbon stream 36 is passed through the chiller section 81 to cool the stream 36 and form a cooled liquid phase hydrocarbon stream 83. In an exemplary embodiment, the cooled liquid phase hydrocarbon stream 83 has a temperature of from about −28 to about 4° C., such as about −12 to about 0° C. and, independently, a pressure of from about 1,890 to about 5,490 kPa gauge.

The cooled, compressed intermediate gas phase stream 80 and the cooled liquid phase hydrocarbon stream 83 are introduced to the absorber 18. As illustrated, in an exemplary embodiment, the cooled, compressed intermediate gas phase stream 80 is introduced to a lower portion of the absorber 18 and rises upwardly while the cooled liquid phase hydrocarbon stream 83 is introduced to an upper portion of the absorber 18 and descends downwardly for countercurrent contact with the rising cooled, compressed intermediate gas phase stream 80. During contact in the absorber 18, $C_3/C_4$ hydrocarbons from the cooled, compressed intermediate gas phase stream 80 are extracted and/or absorbed to the cooled liquid phase hydrocarbon stream 83 to form an $H_2$-rich stream 84 and a cooled intermediate liquid phase hydrocarbon stream 82 that is enriched with $C_3/C_4$ hydrocarbons and further comprises $C_5^+$ hydrocarbons including aromatics. In an exemplary embodiment, the $H_2$-rich stream 84 comprises $H_2$ present in an amount of from about 80 to about 95 mole % with some $C_4^-$ hydrocarbons. In an exemplary embodiment, the cooled intermediate liquid phase hydrocarbon stream 82 has a temperature of from about −28 to about 4° C., such as about −12 to about 0° C., and, independently, a pressure of from about 1,890 to about 5,490 kPa gauge.

In an exemplary embodiment, the cooled intermediate liquid phase hydrocarbon stream 82 is introduced to the stabilizer gas separation zone 23. The cooled intermediate liquid phase hydrocarbon stream is passed through a stabilizer gas separation zone heat exchanger 88 (condenser) for indirect heat exchange with a stabilizer net gas stream 90, which is discussed in further detail below, to form the partially heated intermediate liquid phase hydrocarbon stream 72. In an exemplary embodiment, the partially heated intermediate liquid phase hydrocarbon stream 72 has a temperature of from about 30 to about 100° C. and, independently, a pressure of from about 1,860 to about 5,460 kPa gauge.

As discussed above, the partially heated intermediate liquid phase hydrocarbon stream 72 is passed through the absorption zone heat exchanger 70 to form the partially heated intermediate liquid phase hydrocarbon stream 76. The partially heated intermediate liquid phase hydrocarbon stream 76 is passed through a valve 94 to reduce the pressure of the stream 76 and to form a partially heated intermediate liquid phase hydrocarbon stream 98. In an exemplary embodiment, the partially heated intermediate liquid phase hydrocarbon stream 98 has a temperature of from about 60 to about 150° C. and, independently, a pressure of from about 1,000 to about 1,500 kPa gauge.

The partially heated intermediate liquid phase hydrocarbon stream 98 is passed through a stabilizer heat exchanger 100 for indirect heat exchange with a $C_5^+$ hydrocarbon-rich reformate stream 102, which is discussed in further detail below, to form a heated intermediate liquid phase hydrocarbon stream 104. Optionally, the partially heated intermediate liquid phase hydrocarbon stream 98 may also include a portion from the liquid phase hydrocarbon stream 36 via line 300. In an exemplary embodiment, the heated intermediate liquid phase hydrocarbon stream 104 has a temperature of from about 150 to about 200° C. and, independently, a pressure of from about 900 to about 1,400 kPa gauge.

The heated intermediate liquid phase hydrocarbon stream 104 is passed along to the stabilizer 22. The stabilizer 22 separates the heated intermediate liquid phase hydrocarbon stream 104 into a stabilizer gas stream 106 that comprises $H_2$ and $C_4^-$ hydrocarbons enriched with $C_3/C_4$ hydrocarbons and the $C_5^+$ hydrocarbon-rich reformate stream 102. In an exemplary embodiment, the $C_5^+$ hydrocarbon-rich reformate stream 102 comprises $C_5^+$ hydrocarbons including aromatics present in an amount of about 90 to about 99.9 mole %. As discussed above, the $C_5^+$ hydrocarbon-rich reformate stream 102 is passed through the stabilizer heat exchanger 100 and is removed from the apparatus 10 as a reformate product 107.

The stabilizer gas stream 106 is introduced to the stabilizer gas separation zone 23 and is passed through a first cooler 108 (e.g., an air cooler) and a second cooler 110 (e.g., a water cooler) to partially condense and cool the stream 106 and form a partially condensed stabilizer gas stream 112. In an exemplary embodiment, the partially condensed stabilizer gas stream 112 has a temperature of from about 30 to about 65° C. and, independently, a pressure of from about 800 to about 1,300 kPa gauge.

The partially condensed stabilizer gas stream 112 is passed along to a receiver 114 to remove condensed/liquid hydrocarbons from the stream 112 and to form the stabilizer net gas stream 90 as discussed above and a $C_3^+$ hydrocarbon-containing liquid phase stream 116. The $C_3^+$ hydrocarbon-containing liquid phase stream 116 exits the receiver 114 and is passed along through a pump 118 and a valve 119 back to the stabilizer 22 as a recycle stream.

The stabilizer net gas stream 90 is passed towards the stabilizer gas separation zone heat exchanger 88. Optionally, in an exemplary embodiment, the stabilizer gas separation zone 23 includes a dryer 120 upstream from the stabilizer gas separation zone heat exchanger 88 for removing water from the stabilizer net gas stream 90 to help avoid the formation of hydrates. In an exemplary embodiment, upstream from the stabilizer gas separation zone heat exchanger 88, the stabilizer net gas stream 90 includes water present in an amount of about 15 ppm by weight or greater, and after being passed through the dryer 120, the stabilizer net gas stream 90 includes water present in an amount of less than about 15 ppm by weight.

As discussed above, the stabilizer net gas stream 90 is passed through the stabilizer gas separation zone heat exchanger 88 for indirect heat exchange with the cooled intermediate liquid phase hydrocarbon stream 82 to partially condense and cool the stream 90 and to form a partially condensed stabilizer net gas stream 122. Although the stabilizer net gas stream 90 is shown as being passed through only a single stabilizer gas separation zone heat exchanger 88, the stream 90 may be partially condensed and cooled by being advanced through one or more heat exchangers, chillers, coolers, or combination thereof. In an exemplary embodiment, the partially condensed stabilizer net gas stream 122 has a temperature of from about −28 to about 4° C., for example, from about −12 to about 0° C. and, independently, a pressure of from about 700 to about 1,200 kPa gauge.

The partially condensed stabilizer net gas stream 122 is introduced to a separator 124. The separator 124 may be configured as a flash drum, or alternatively, may be configured as a multi-stage fractionation tower. The separator 124 separates $C_3/C_4$ hydrocarbons and any remaining $H_2$ and $C_2^-$ hydrocarbons from the partially condensed stabilizer net gas stream 122 to form the light ends gas stream 126 and a $C_3/C_4$ hydrocarbon-rich LPG stream 128. In an exemplary embodiment, the $C_3/C_4$ hydrocarbon-rich LPG stream 128 comprises $C_3/C_4$ hydrocarbons present in an amount of about 70 to about 99.9 mole % and the light ends gas stream 126 comprises $H_2$ present in an amount of from about 1 to about 50 mole %, $C_2^-$ hydrocarbons present in an amount of from about 20 to about 60 mole %, and some $C_3^+$ hydrocarbons. As illustrated, the $C_3/C_4$ hydrocarbon-rich LPG stream 128 is passed through a pump 130 and is optionally combined with a side stream 132 of the $C_3^+$ hydrocarbon-containing liquid phase stream 116 and is removed from the apparatus 10 as an LPG product stream. The light ends gas stream 126 is removed from the apparatus 10 to be used, for example, as fuel gas.

Figure 2:
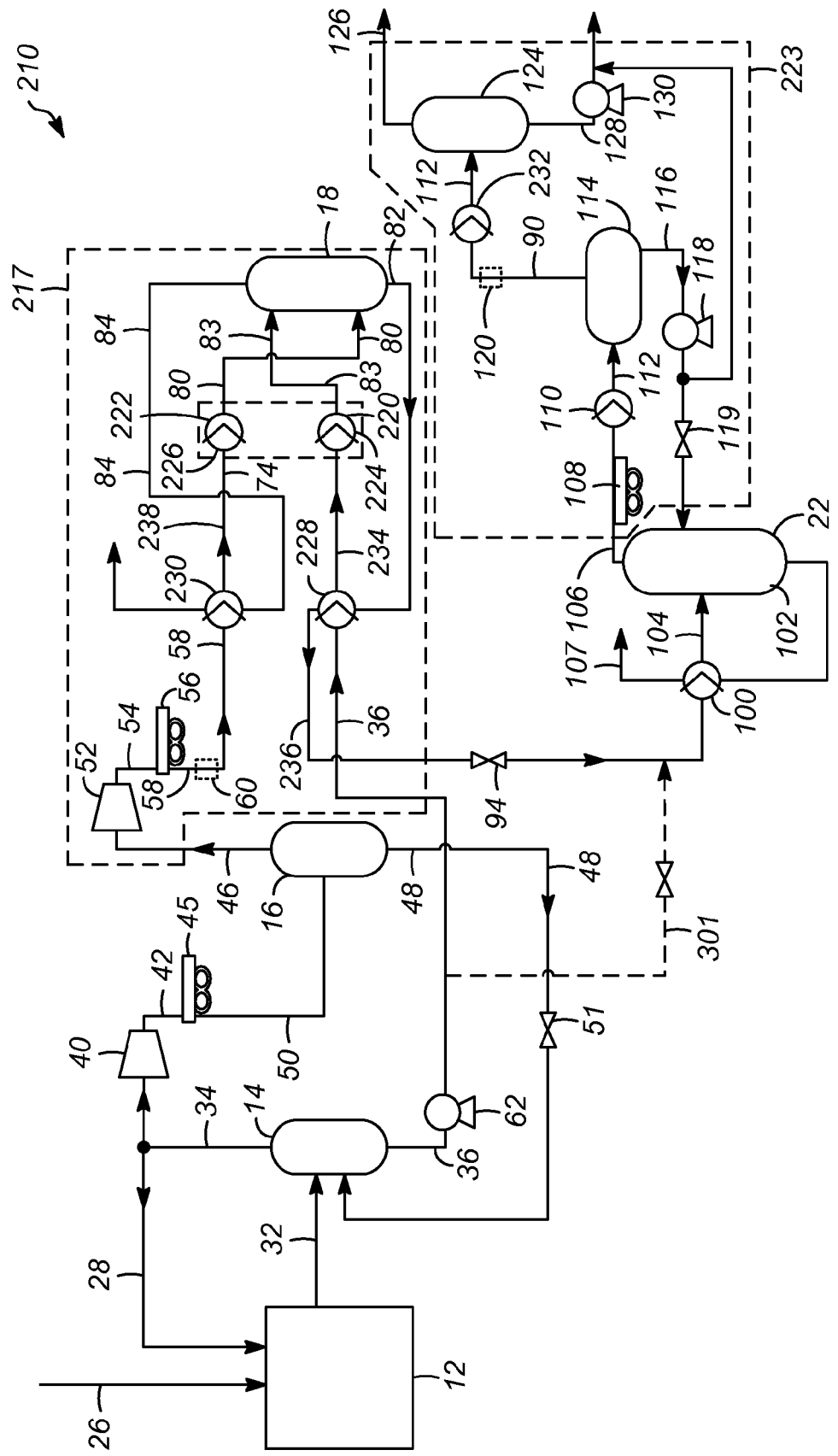
FIG. 2 schematically illustrates an apparatus and a method for reforming of hydrocarbons including recovery of products in accordance with another exemplary embodiment.

Referring to FIG. 2, an apparatus 210 for reforming of hydrocarbons in accordance with another exemplary embodiment is provided. The apparatus 210 is similarly configured to the apparatus 10 including the reforming zone 12, the separation zone 14, the knockout drum 16, an absorption zone 217 including the absorber 18, the stabilizer 22, and a stabilizer gas separation zone 223 as discussed above in relation to FIG. 1 with the exception that the absorption zone 217 includes two separate chillers 220 and 222 and two separate absorption zone heat exchangers 228 and 230 and the stabilizer gas separation zone 223 includes a condenser/chiller 232. As illustrated, the chillers 220 and 222 have corresponding chiller sections 224 and 226.

In particular, in the absorption zone 217, the liquid phase hydrocarbon stream 36 is introduced to the absorption zone heat exchanger 228 for indirect heat exchange with the cooled intermediate liquid phase hydrocarbon stream 82 to form a partially cooled liquid phase hydrocarbon stream 234 and a partially heated intermediate liquid phase hydrocarbon stream 236. In an exemplary embodiment, the partially cooled liquid phase hydrocarbon stream 234 has a temperature of from about 10 to about 40° C., and independently, a pressure of from about 1,920 to about 5,520 kPa gauge. In an exemplary embodiment, the partially heated intermediate liquid phase hydrocarbon stream 236 has a temperature of from about 60 to about 150° C., and independently, a pressure of from about 1,860 to about 5,460 kPa gauge.

The partially heated intermediate liquid phase hydrocarbon stream 236 is passed through the valve 94 and is introduced to the stabilizer heat exchanger 100 to form the heated intermediate liquid phase hydrocarbon stream 104 as discussed above. Optionally, a portion of the liquid phase hydrocarbon stream 36 may be combined with the partially heated, intermediate liquid phase hydrocarbon stream 236 upstream of the heat exchanger 100 via line 301. The partially cooled liquid phase hydrocarbon stream 234 is introduced to the chiller 220 and is passed through the chiller section 224 to form the cooled liquid phase hydrocarbon stream 83 as discussed above.

In an exemplary embodiment, the partially cooled, compressed intermediate gas phase stream 58 exits the cooler 56 and is optionally passed through the dryer 60 and introduced to the absorption zone heat exchanger 230. In the absorption zone heat exchanger 230, heat is indirectly exchanged between the partially cooled, compressed intermediate gas phase stream 58 and the $H_2$-rich stream 84 prior to removing the $H_2$-rich stream 84 from the apparatus 210 to form a partially cooled, compressed intermediate gas phase stream 238. In an exemplary embodiment, the partially cooled, compressed intermediate gas phase stream 238 has a temperature of from about 10 to about 40° C., and independently, a pressure of from about 1,920 to about 5,520 kPa gauge. The partially cooled, compressed intermediate gas phase stream 238 is introduced to the chiller 222 and is passed through the chiller section 226 to form the cooled, compressed intermediate gas phase stream 80. As discussed above, the cooled, compressed intermediate gas phase stream 80 and the cooled liquid phase hydrocarbon stream 83 are introduced to the absorber 18 to form the $H_2$-rich stream 84 and a cooled intermediate liquid phase hydrocarbon stream 82 that is enriched with $C_3/C_4$ hydrocarbons and further comprises $C_5^+$ hydrocarbons including aromatics.

In the stabilizer gas separation zone 223, the stabilizer net gas stream 90 is passed optionally through the dryer 120 to the condenser/chiller 232. The condenser/chiller 232 partially condenses and cools the stabilizer net gas stream 90 to form the partially condensed stabilizer gas stream 112. As discussed above, the partially condensed stabilizer gas stream 112 is separated in the separator 124 into the light ends gas stream 126 and the $C_3/C_4$ hydrocarbon-rich LPG stream 128.

Accordingly, apparatuses and methods for reforming of hydrocarbons with improved recovery of products from a reforming-zone effluent have been described. The exemplary embodiments taught herein separate a reforming-zone effluent in a separation zone to form a net gas phase stream and a liquid phase hydrocarbon stream. The net gas phase stream is compressed, partially condensed and cooled to form a partially condensed, compressed net gas phase stream. The partially condensed, compressed net gas phase stream is separated in a knockout drum to form an intermediate gas phase stream. In an exemplary embodiment, in an absorption zone, the intermediate gas phase stream is cooled to form a cooled intermediate gas phase stream. The liquid phase hydrocarbon stream is cooled to form a cooled liquid phase hydrocarbon stream. The cooled intermediate gas phase stream is contacted with the cooled liquid phase hydrocarbon stream in an absorber to form an $H_2$-rich stream and a cooled second intermediate liquid phase hydrocarbon stream that is enriched with $C_3/C_4$ hydrocarbons. The cooled second intermediate liquid phase hydrocarbon stream is further separated to form a $C_5^+$ hydrocarbon-rich reformate stream, a light ends gas stream, and a $C_3/C_4$ hydrocarbon-rich LPG stream.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

What is claimed is:

1. An apparatus for reforming of hydrocarbons including recovery of products, the apparatus comprising:
   a separation zone configured to receive and separate a reforming-zone effluent that comprises $H_2$, $C_4^-$ hydrocarbons, and $C_5^+$ hydrocarbons including aromatics to form a net gas phase stream that comprises $H_2$ and $C_6^-$ hydrocarbons and a liquid phase hydrocarbon stream that comprises $C_5^+$ hydrocarbons;
   a first compressor configured to receive and compress the net gas phase stream to form a compressed net gas phase stream;
   a first cooler configured to receive and partially condense and cool the compressed net gas phase stream to form a partially condensed, compressed net gas phase stream;

a knockout drum configured to receive and separate the partially condensed, compressed net gas phase stream into an intermediate gas phase stream and a first intermediate liquid phase hydrocarbon stream;

a first chiller section configured to receive and cool the intermediate gas phase stream to form a cooled intermediate gas phase stream;

a second chiller section configured to receive and cool the liquid phase hydrocarbon stream to form a cooled liquid phase hydrocarbon stream; and an absorber in fluid communication with the first chiller section and the second chiller section to correspondingly receive the cooled intermediate gas phase stream and the cooled liquid phase hydrocarbon stream, wherein the absorber is configured for contacting the cooled intermediate gas phase stream with the cooled liquid phase hydrocarbon stream to extract $C_3/C_4$ hydrocarbons from the cooled intermediate gas phase stream to the cooled liquid phase hydrocarbon stream and to form an $H_2$-rich stream and a cooled second intermediate liquid phase hydrocarbon stream that is enriched with $C_3/C_4$ hydrocarbons and further comprises $C_5^+$ hydrocarbons.

2. The apparatus of claim 1, wherein the separation zone is configured to receive the first intermediate liquid phase hydrocarbon stream as a recycle stream for further separation.

3. The apparatus of claim 1, further comprising:

at least one heater, heat exchanger, or combinations thereof configured to receive and heat the cooled second intermediate liquid phase hydrocarbon stream to form a heated second intermediate liquid phase hydrocarbon stream;

a stabilizer configured to receive and separate the heated second intermediate liquid phase hydrocarbon stream to form a $C_5^+$ hydrocarbon-rich reformate stream that comprises primarily $C_5^+$ hydrocarbons and a stabilizer gas stream that comprises $H_2$ and $C_4^-$ hydrocarbons; and a stabilizer gas separation zone configured to receive and partially condense and cool at least a portion of the stabilizer gas stream to form a partially condensed stabilizer net gas stream, wherein the stabilizer gas separation zone comprises:

a separator configured to receive and separate the partially condensed stabilizer net gas stream to form a $C_3/C_4$ hydrocarbon-rich LPG stream that comprises primarily $C_3/C_4$ hydrocarbons and a light ends gas stream that comprises $H_2$ and $C_2^-$ hydrocarbons.

4. The apparatus of claim 3, wherein the stabilizer gas separation zone comprises at least one heat exchanger, chiller, cooler, or combination thereof configured to receive and partially condense and cool the at least the portion of the stabilizer gas stream to form the partially condensed stabilizer net gas stream.

5. The apparatus of claim 4, wherein the at least one heat exchanger, chiller, cooler, or combination thereof is a stabilizer gas separation zone heat exchanger configured for indirect heat exchange between the cooled second intermediate liquid phase hydrocarbon stream and the at least the portion of the stabilizer gas stream to form a partially heated, second intermediate liquid phase hydrocarbon stream and the partially condensed stabilizer net gas stream, respectively, wherein the at least one heater, heat exchanger, or combinations thereof comprises the stabilizer gas separation zone heat exchanger and at least one additional heater, heat exchanger, or combinations thereof that is configured to receive and heat the partially heated, second intermediate liquid phase hydrocarbon stream to form the heated second intermediate liquid phase hydrocarbon stream.

6. The apparatus of claim 5, further comprising:

an absorption zone heat exchanger that is configured for indirect heat exchange between the intermediate gas phase stream and the partially heated, second intermediate liquid phase hydrocarbon stream to form a further partially cooled, compressed intermediate gas phase stream and a further partially heated, second intermediate liquid phase hydrocarbon stream, respectively, wherein the first chiller section is configured to receive and cool the further partially cooled, compressed intermediate gas phase stream to form the cooled intermediate gas phase stream; and a stabilizer heat exchanger that is configured for indirect heat exchange between the further partially heated, second intermediate liquid phase hydrocarbon stream and the $C_5^+$ hydrocarbon-rich reformate stream to form the heated second intermediate liquid phase hydrocarbon stream, wherein the at least one additional heater, heat exchanger, or combinations comprises the absorption zone heat exchanger and the stabilizer heat exchanger.

7. The apparatus of claim 4, wherein the stabilizer gas separation zone comprises a dryer that is upstream from the at least one heat exchanger, chiller, cooler, or combination and is configured to remove water from the portion of the stabilizer gas stream before the portion of the stabilizer gas stream is introduced to the at least one heat exchanger, chiller, cooler, or combination.

8. The apparatus of claim 1, further comprising a dryer that is upstream from the first chiller section and is configured to remove water from the intermediate gas phase stream before the intermediate gas phase stream is introduced to the first chiller section.

9. The apparatus of claim 1, further comprising:

a second compressor configured to receive and compress the intermediate gas phase stream to form a compressed intermediate gas phase stream; and a second cooler configured to receive and partially cool the compressed intermediate gas phase stream to form a partially cooled, compressed intermediate gas phase stream, wherein the first chiller section is configured to receive and cool the partially cooled, compressed intermediate gas phase stream to form the cooled intermediate gas phase stream.

10. The apparatus of claim 9, further comprising a heat exchanger for indirect heat exchange between the partially cooled, compressed intermediate gas phase stream and the $H_2$-rich stream to form a further partially cooled, compressed intermediate gas phase stream, wherein the first chiller section is configured to receive and cool the further partially cooled, compressed intermediate gas phase stream to form the cooled intermediate gas phase stream.

* * * * *